United States Patent [19]

Gleason

[11] Patent Number: 4,626,271
[45] Date of Patent: Dec. 2, 1986

[54] CYANOBACTERIN HERBICIDE

[75] Inventor: Florence K. Gleason, Chaska, Minn.

[73] Assignee: The Regents of the University of Minnesota, Minneapolis, Minn.

[21] Appl. No.: 776,842

[22] Filed: Sep. 17, 1985

[51] Int. Cl.$^4$ ............................................. A01N 43/08
[52] U.S. Cl. ......................................... 71/66; 71/88; 71/67
[58] Field of Search ...................................... 71/66, 88

[56] References Cited

U.S. PATENT DOCUMENTS 4,402,971  9/1983  Edwards ............................. 424/279

OTHER PUBLICATIONS

Science, vol. 215, Jan. 22, 1982, pp. 400–402, "Isolation of Chlorine Containing Antibiotic From the Freshwater Cyanobacterium *Scytonema hoffmanni*," by C. P. Mason et al.
Arch Microbiol (1984) "Site of Action of the Natural Algicide, Cyanobacterin, in the Blue–Green Alga, Synechococcus sp.", by Florence Gleason et al.
"Blue–Green Algal (Cyanophyta) Toxins", from *The Minnesota Academy of Science*, by Charles P. Mason.
"Determination of Blue–Green Algal (Cyanophyta) Toxins", from *J. Phycol.* (Jun. 1979), by C. P. Mason and F. K. Gleason.
*The Minnesota Chemist*, Apr., 1981, "Isolation of Characterization of a Naturally–Occurring Algicide from the Blue–Green Alga, Scytonema hoffmanni", by Florence Gleason.
News Release, from Minnesota Sea Grant College Program, May 23, 1985, "Algae: A New Source of Herbicides".
"Activity of the Natural Algicide, Cyanobacterin, on Eukaryotic Microorganisms", by Gleason and Baxa.
"Total Synthesis and X-Ray Structure Determination of Cyanobacterin," Internal Organic Chemistry, vol. 49, No. 4, (1984) by Williard and Porwoll.

*Primary Examiner*—Catherine L. Mills
*Attorney, Agent, or Firm*—Vidas & Arrett

[57] ABSTRACT

An herbicidal composition comprising cyanobacterin and a surfactant. Cyanobacterin obtained from extracts of blue-green algae or chemical synthesis when combined with a sticker such as non-ionic surfactants provides an herbicidal formulation which will adhere to green plants in a herbicidally effective amount.

6 Claims, No Drawings

CYANOBACTERIN HERBICIDE

DESCRIPTION

Field of the Invention

This invention relates to herbicides and methods of using same, and more particularly, to cyanobacterin containing compounds and their use on higher plants.

Background of the Invention

It has been known for many years that some organisms produce compounds which are toxic to other organisms. The discovery that the antimicrobial compound penicillin is produced by penicillium mold is one such example.

More recently, it has been discovered that life forms other than bacteria and fungi produce biocidal compounds. Most of the antimicrobial compounds previously reported have been produced by marine algae, principally the red and brown algae. Some antibiotic substances have been reported in fresh water chlorophytes and they also occur in the cyanobacteria. Toxin production by cyanophytes (blue-green algae) has been demonstrated by feeding large quantities of algae to vertebrates. It has also been demonstrated by noting that growth metabolites of some algae inhibit the growth of other algae.

The inventor and others first discovered the antimicrobial properties of the blue-green alga *Scytonema hofmanni* while attempting to grow the organism with other species of algae in laboratory cultures. Within 7 to 10 days, *S.hofmanni* had cleared the area and its vicinity of other algae against which it was paired. Extracts of this fresh water cyanophyte were found to inhibit the growth of some procaryotes, such as *Bacillus brevis*, *Aphanocapsa* and *Synechococcus*. Growth was found to be promoted by the addition of salt-free extract to cultures of *Streptomyces epidermidis* and *Nocardia asteroides*.

Potent antibiotic activity of the substance released by *S.hofmanni* was indicated since a crude extract protein (as little as 30 micrograms per ml) inhibited the growth of Synechococcus sp. (ATCC 27146.). A purified antibiotic was characterized by several analytical techniques. The description of the compound, since named cyanobacterin, is described in U.S. Pat. No. 4,402,971 to Edwards. That patent states that cyanobacterin is usable against blue-green algae and has apparent bacteriocidal activity. The Edwards patent states that there is apparent algicidal activity against green algae, but that cyanobacterin would probably not harm desirable plants and animals.

BRIEF SUMMARY OF THE INVENTION

The inventor has found that cyanobacterin may be used to inhibit the growth of higher forms of life. This is in direct contrast to the early evidence that cyanobacterin damage the outer cell walls of procaryotic organisms. The inventor has found that cyanobacterin apparently is not limited to use against organisms having procaryotic or procaryotic-like cell wall compositions. Cyanobacterin is not like penicillin which may only act against procaryotes due to its action against peptidoglycan, a constituent found only in procaryotes.

The inventor has discovered that cyanobacterin is an effective herbicide for both monocotyledonous and dicotyledonous angiosperms when properly applied. As used herein, "herbicide" includes herbistatic.

The cyanobacterin is prepared for use by including a "sticker" which affixes the compound to the plants treated. It was found that when "sticker free" cyanobacterin is applied to plants, it tends to "bead up" and roll off which severely limits its usefulness. "Stickers" which were found to be usable to affix the herbicide to the plants include water soluble nonionic surfactants. Suitable surfactants include spreaders for use as spray adjuvants such as Chevron Chemical Company's X-77 ® Spreader, the Rohm & Haas Tritons ® and the Atlas Company's Tweens ®. The combined action of the cyanobacterin and some nonionic surfactacts increases the herbicidal action.

The composition may be formulated from high purity cyanobacterin or from crude extracts obtained from the blue-green algae since high purity is not required. Broad-leaved plants were found to be most sensitive to the cyanobacterin. As little as one part of the cyanobacterin to 450 parts of the plant to be treated by dry weight may be effective as a herbicide. Additionally, the composition may be formulated from a synthetic cyanobacterin, such as the racemic mixture described by T. T. Jong et al, "Total synthesis and X-ray structure determination of cyanobacterin", J. Org. Chem. 49:735–736(1984).

DETAILED DESCRIPTION OF THE INVENTION

The cyanobacterin used in this invention may be obtained from *Scytonema hofmanni* (UTEX 2349 University of Texas Collection, Austin, Tex.) cells. Cyanobacterin is a diaryl substituted gamma-ylidene, gamma-butyro lactone with a chlorine substituent on one of the aromatic rings. The cyanobacterin analog, anhydrocyanobacterin has no biological activity although it is structurally similar to the parent compound. This compound results from dehydration of the parent compound:

The inventor found that this anyhydro compound has no effect on cell growth. It has been postulated by the inventor that a hydrophilic constituent on the lactone ring is crucial to the activity of cyanobacterin and may be involved in protein binding.

It is theorized that cyanobacterin acts on green plants by specifically binding to some component of the photosynthetic electron transport system. Cyanobacterin inhibits electron flow from water to electron acceptors suggesting that its site of action is in photosystem II.

Cyanobacterin may be obtained by extraction from *Scytonema hofmanni* cells or its growth medium with a liquid organic solvent such as diethylether. Purified cyanobacterin may be obtained by subjecting the crude extract to at least one chromatographic separation procedure. The compound is usable as a crude cellular extract or purified, crystalline form. It may be dispersed in ether solution and many organic solvents in order to be utilized in a solution form.

Concentrate obtained from cell fragments of the blue-green algae which has been centrifuged to remove cell debris has been found to be an active herbicide.

Synthetic cyanobacterin such as the racemic mixture prepared by Jong T. T. et al in *J. Org. Chem.* 49:735–736(1984) may be utilized as an herbicide although it has only about half the activity of cyanobacterin in a cyanobacterial spheroplast system. It has the same activity in whole cell growth measurements based on long term studies.

Before cyanobacterin may be effective as a terrestrial herbicide, it must be mixed with a surfactant "sticker". The composition includes a surfactant in order to adhere to the surface of the green plants so treated. Non-ionic surfactants such as the Ortho X-77 ® Spreader of Chevron Chemical Company are suitable. The X-77 ® water-soluble, non-ionic surfactant includes alkylaryl-polyoxyethlene, glycols, free fatty acids and isopropanol as its principal functioning agents. Nearly any compound which provides quick wetting and more uniform and increased coverage and retention when sprayed on a plant may be employed in the invention. Tritons of Rohm & Haas Chemical Company, such as Triton X-100, a polyethylene glycol p-isooctylphenyl ether and Triton N, a nonoxynol are good, nonionic surfactants which provide reduced surface tension for spray droplets containing cyanobacterin. Other usable stickers include Regulard surfactants of Colloidal Products Corp., Tween 20, 40 and 80 surfactants of Atlas Chemical Company and "Science Spreader" of Science Products Co. of Chicago, Ill.

PREPARATION OF HERBICIDAL COMPOUND

The herbicidal compound of the invention may be obtained by combining cyanobacterin with a surfactant. Even crude cellular extracts containing cyanobacterin are useful in the invention. However, most testing was conducted using purified ether extracts of cyanobacterin in order to better quantify the herbicidal properties of the composition.

EXAMPLE I 10 mg of cyanobacterin dissolved in 1ml. of ethyl ether was mixed with 0.1 ml of the Science "Sticker" of Science Products, Co., which contains about 77% Triton B-1956 brand surfactant. 10 ml of water was added and mixed. After mixing for about 30 minutes to allow the ether to evaporate, the composition was ready to apply to plants.

EXAMPLE II 25 mg of cyanobacterin dissolved in about 1ml of ethyl ether was added to 5 ml of a 1:80 dilution of Ortho X-77 brand surfactant in water. After mixing, 85 ml of water was slowly added until a dilution of 1:1360 (sticker: water) was obtained. The sticker is below phytotoxic levels at this concentration so any herbicidal action is due to the cyanobacterin. Again, the ether is allowed to evaporate before applying to plants.

Use Against Aquatic Plants

The effect of cyanobacterin was initially tested on the aquatic angiosperms, Lemna gibba, L.minor and Lemna 6746 (Duckweed). Cyanobacterin stopped frond multiplication at a minimum dose of 0.5 $\mu$g per ml of growth medium (1.1 $\mu$M). The plants recovered after about 7–12 days. Presumably, this is due to degradation of the cyanobacterin over time which drops the dosage below the minimum. At a concentration of 1.0 $\mu$g/ml (2.3 $\mu$M), cyanobacterin is toxic to Lemna. The plants generally appear normal for 10–15 days after which the roots fall off and the leaves become chlorotic. By 30 days, most plants treated with 1.0 $\mu$g/ml or greater concentrations of purified cyanobacterin were dead.

Use Against Terrestrial Plants

A variety of green plants were treated with a cyanobacterin solution prepared in accordance with Example I above. An atomizer was used to spray the plants with a fine spray. Before placing the fluid into an atomizer, the solution was measured and then remeasured after application on the plants. The difference in levels showed the amount of solution applied to the plants.

A control solution of 0.1 ml of sticker-ether in 10 ml of distilled water was applied to the control plants. These plants were treated in the same manner as in the cyanobacterin application and measured in the same way. Plants were cut off at the soil line and dried for 16 hours at 110° C.

Sweet Corn

Zea Mays of the hybrid variety Goldencross Bantam was tested with one plant per pot. A total of nine control plants were used and 14 plants were treated with the cyanobacterin composition of Example I. The plants were treated once, 8 days after germination. After growing for a total of 15 days after treatment, the plants were cut off at the soil line and the dry weight was determined. A control plant dry weight was 227.4 milligrams and the cyanobacterin treated plant dry weight was 59.4 milligrams. The amount of cyanobacterin utilized was 1.0 milligrams.

On the ninth day after treatment the plants showed no new growth. The leaves were curling along the margins and were browning. By the fifteenth day the cyanobacterin treated plants were dead. Similar effects were noted at higher concentrations of cyanobacterin but with a mottled chlorotic effect showing about 5 or 6 days after treatment. Some of the plants were not dead at the kill date but all treated plants were stunted in growth when compared to control plant heights.

Pea

Pisum sativum, var. Little Marvel, plants were tested at a rate of 1 and 2 plants per pot. With one plant per pot, a total of nine control plants were used and 12 cyanobacterin treated plants were utilized. With 2 plants per pot, one control plant was utilized and 2 cyanobacterin treated plants were utilized. The plants were treated 8 and 6 days after germination respectively, with the cyanobacterin compound of Example I. The pots containing 1 plant per pot were treated with 1.5 milligrams and the pots containing 2 plants were treated with 0.6 milligrams of the cyanobacterin compound. The control plant dry weight of a single plant per pot plants after the fifteen days of growth was 363.8 milligrams and 194.9 milligrams for the cyanobacterin treated plant dry weight. The plants in the pots containing two plants per pot had a control plant dry weight of 169.8 milligrams and a cyanobacterin treated plant dry weight of 101.4 milligrams.

By the fourth day after treatment, all cyanobacterin treated plants were showing sensitivity to the material. By the 11th day the smaller plants were dead while the larger plants' leaves were chlorotic, wilted or dead. On the 15th day all of the cyanobacterin treated plants were dead but the control treated plants were healthy. The overall effect of the cyanobacterin concentration level appears to be the same from a low of 0.6 milligrams to 1.5 milligrams of material per plant.

Curled Dock

Rumex crispus was grown at a rate of 10 plants or more per pot. A total of 5 control pots were used and 5 pots were treated with the cyanobacterin containing compound of Example I. Seven days after germination the plants were treated with 1.45 milligrams of cyanobacterin. On the second day after treatment, half of the plants were curled and had a cyanobacterin effect. By the 9th day, half the plants were dead and half were chlorotic. By the 15th day all were dead except for a few and these were approximately one-quarter the size of the control plants. The control plant dry weight at the fifteenth day was 453.3 milligrams and the cyanobacterin dry weight was 93.1 milligrams.

Curled dock plants were also treated with 0.5 milligrams of cyanobacterin. The plants were treated with the cyanobacterin compound 8 days after germination. On the 7th day after treatment, many of the plants were dead and others were chlorotic. By the 15th day, half of the plants were dead, one-quarter were chlorotic and one-quarter were large, green and healthy like the control. At the fifteenth day, the plants had a control plant dry weight of 451.9 milligrams and a cyanobacterin treated plant dry weight of 239.1 milligrams.

Wild Buckwheat

Polygonium convolvulus plants were raised at a rate of over 10 plants per pot. Five control pots were used and 5 pots were treated with the cyanobacterin containing compound of the invention.

The first plants treated were treated 2 days after germination with 0.29 milligrams of the cyanobacterin. The control plant dry weight at the fifteenth day was 92.4 milligrams and the cyanobacterin treated dry weight was 59.1 milligrams. The second group of plants were treated 4 days after germination with 0.5 milligrams of cyanobacterin. They had a control plant dry weight at the fifteenth day of 157.8 milligrams and cyanobacterin treated plant dry weight of 59.1 milligrams.

Only a few of the cyanobacterin treated plants were dead by the 15th day of the experiment. Most of the plants treated with either concentration were still alive at the end of the experiment. It was noted that at the higher dose, the plants died earlier and had a more chlorotic coloration than the plants at the lower concentration.

Wild Oats

Avena fatua plants were grown at a rate of over 10 plants per pot. A total of 5 control pots were used and 5 cyanobacterin treated pots were utilized.

Three separate concentrations of cyanobacterin were utilized. In group 1 the plants were treated 3 days after germination with 0.44 milligrams of the cyanobacterin. The plants after cutting down fifteen days after treatment had a control plant dry weight of 154.6 milligrams and a cyanobacterin treated plant dry weight of 115.5 milligrams. A second group were treated with 0.6 milligrams of cyanobacterin two weeks after germination. That group had a control plant dry weight of 328.5 milligrams and a cyanobacterin treated plant dry weight of 79.5 milligrams fifteen days after treatment. The third group of plants were treated with 1.05 milligrams of cyanobacterin 7 days after germination. This group had a control plant dry weight at the fifteenth day of 489.6 milligrams and a cyanobacterin treated dry weight of 155.8 milligrams.

At approximately the 8th day after treatment, all of the leaves on the cyanobacterin treated leaves were yellowing at the tips. This was still the case at the end of the experiment. The leaves were stressed but overall were still green and growing. Below 0.6 milligrams, the plants seemed to be effected little and at higher concentrations the effect appeared to be about the same.

Green Foxtail

Setaria viridis plants were grown at a rate of over 10 per pot. A total of 5 control pots were used and 5 cyanobacterin treated pots were utilized. Two concentrations of cyanobacterin were utilized. In the first group 0.5 milligrams of cyanobacterin was applied to plants 8 days after germination. The control plant dry weight on the fifteenth day after cutting was 365.8 milligrams and the cyanobacterin treated plant dry weight was 176.3 milligrams. A second group of plants was treated with 2.8 milligrams of cyanobacterin 7 days after germination. That group had a control plant dry weight on the fifteenth day after cutting of 411.7 milligrams and a cyanobacterin treated plant dry weight of 217.7 milligrams.

At approximately the 9th day after treatment, approximately half of the plants had died. At 15 days, the surviving plants were found to be green or chlorotic in varied degrees and were found to be smaller than the control plants.

Cyanobacterin, when applied to the soil had no effect. The compound is very hydrophobic and may adhere to soil particles. Also, it may not be transported through the root vascular system. The Hill reaction is inhibited by cyanobacterin as shown by the use of photosynthetically active pea chloroplasts. Cyanobacterin completely inhibits oxygen evolution at a concentration of 110 nM in the presence of DCPIP, a concentration which is comparable to the known photosystem II inhibitor, DCMU.

Cyanobacterin, as an inhibitor of photosynthetic election transport is an effective, natural herbicide which may be derived from the cyanophyte *S.hofmanni* or from laboratory synthesis. This surprising herbicidal activity may be employed to all aquatic and terrestrial angiosperms.

In considering this invention, it must be remembered that the disclosure is illustrative only, and that the scope of the invention is to be determined by the appended claims.

What is claimed is:

1. A method for inhibiting the growth of plants comprising the step of exposing the plant to a composition comprising cyanobacterin and a surfactant in a growth inhibiting effective amount.

2. A method for inhibiting the growth of eucaryotic green plants comprising the steps of exposing the plants to a composition comprising cyanobacterin and a surfactant in a growth-inhibiting effective amount.

3. A method for killing plants comprising:
   (a) applying a composition comprising cyanobacterin and a surfactant to the leaves of the plant.

4. A method for inhibiting the growth of aquatic angiosperms on a surface of water comprising the step of spraying a composition comprising cyanobacterin in a herbicidally effective amount over the upper surface of aquatic angiosperms floating on a body of water.

5. The method of claim 4 wherein said composition is applied to duckweed at a concentration of greater than 1.0 micrograms cyanobacterin per ml of water in the body of water.

6. A method for inhibiting the growth of green plants comprising the step of exposing the plant to a composition comprising cyanobacterin in a growth inhibiting effective amount and a surfactant such that the photosynthetic electron transport system of the plant is inhibited.

* * * * *